United States Patent [19]

Schwengers

[11] Patent Number: 4,927,756

[45] Date of Patent: May 22, 1990

[54] WATER SOLUBLE IRON DEXTRAN AND A PROCESS FOR ITS MANUFACTURE

[75] Inventor: Dieter Schwengers, Dormagen, Fed. Rep. of Germany

[73] Assignee: Pfeifer & Langen, Cologne, Fed. Rep. of Germany

[21] Appl. No.: 159,146

[22] Filed: Feb. 25, 1988

Related U.S. Application Data

[62] Division of Ser. No. 741,395, Jun. 5, 1985, Pat. No. 4,749,695.

[30] Foreign Application Priority Data

Jun. 15, 1984 [DE] Fed. Rep. of Germany ....... 3422249

[51] Int. Cl.$^5$ .................. C12P 19/08; C12P 19/18; C08B 37/02; C07G 17/001
[52] U.S. Cl. ..................................... 435/103; 435/97; 536/112; 536/113; 536/114
[58] Field of Search .................. 435/103, 822, 97; 536/112, 113, 114; 514/59

[56] References Cited

U.S. PATENT DOCUMENTS

| | | | |
|---|---|---|---|
| Re. 27,240 | 11/1971 | London et al. ............... | 424/147 |
| 4,101,435 | 7/1978 | Hasegawa et al. ........... | 536/113 |
| 4,180,567 | 12/1979 | Herb ........................ | 514/59 |
| 4,673,643 | 6/1987 | Schwengers ................. | 435/103 |

*Primary Examiner*—Johnnie R. Brown
*Assistant Examiner*—Pamela S. Webber
*Attorney, Agent, or Firm*—Sprung Horn Kramer & Woods

[57] ABSTRACT

A water-soluble iron dextran having a high iron content is prepared by adding to an aqueous solution containing more than 200 mmol D-glucose per 1000 U$\alpha$(1→6)-D-glucosyltransferase, at 265 to 310 K and a pH value of 4.5 to 8, an aqueous sucrose solution in a mole ratio of sucrose to glucose of from 2.0 to 5.0; separating, after the consumption of the sucrose, glucose, liberated fructose and undesired oligosaccharides; reacting the so-purified dextran, having an average molar mass of from 2000 to 4000, with freshly precipitated iron(III) hydroxide and, if desired, further purifying the same.

Iron dextrans having an iron content of from 27 to 33 percent by weight and an average molar mass of the dextran component of from 2000 to 4000, may be prepared according to the process of the invention which can be used in the treatment of iron deficiency.

17 Claims, No Drawings

WATER SOLUBLE IRON DEXTRAN AND A PROCESS FOR ITS MANUFACTURE

This is a division of application Ser. No. 741,395, filed June 5, 1985, now U.S. Pat. No. 4,749,695.

Iron dextran preparations are primarily injected in veterinary medicine, intravenously and intramuscularly, for the treatment of anemia resulting from iron deficiency. The preparations are manufactured as dextran complex by reaction with colloidal iron (III) hydroxide.

High requirements are set on the stability of the solution and the bio-availability of the iron, in particular when the preparations are designed to be administered intravenously. When iron dextrans have a high iron content, i.e. 20 percent and more iron per gram of dry substance, these requirements cannot be fulfilled when dextrans having a too high average molecular weight are used for the manufacture. As a result of intermolecular complex formation via the iron atoms between various dextran molecules, gels and precipitates are formed. For this reason, dextrans having a low molecular weight of from 4000–6000 are normally used for the synthesis of iron dextran. Dextrans of this molecular weight range are obtained by acid hydrolysis of high molecular weight native dextran and are produced, for example, in the preparation of clinical dextrans having an average molecular weight of from 40000–75000 as by-product.

The molecular weight distribution of these "waste dextrans" is, however, very broad and usually extends from glucose up to molecular weights of about 50000. It is, therefore, conventional practice to free the raw iron dextran, obtained by reacting dextran and Fe(III) salts under alkaline conditions, by complicated precipitation-fractionations with solvents or by membrane separation processes, from the undesirable higher molecular weight components.

If the waste fractions in the preparation of clinical dextran contain too much glucose and iso-maltooligosaccharides up to a molecular weight of about 1,000, these saccharides will likewise have to be removed prior to the reaction to iron dextran because they substantially decompose under the reaction conditions to form toxic products.

It would be desirable, for the reasons mentioned above, to prepare a water soluble iron dextran having a high iron content which, on the other hand, means that dextrans having an average molecular weight of from 2000 to 4000, with a narrow molecular weight distribution must be available.

This problem is solved by the process of this invention which is characterized by adding to an aqueous solution containing more than 200 mmol D-glucose per 1000 U $\alpha(1\rightarrow 6)$-D-glucosyl transferase, at 265 to 310 K. and a pH value of 4.5, an aqueous solution of sucrose, in such an amount that the mole ratio of sucrose to glucose is from 2.0 to 5.0; separating after the consumption of the sucrose the glucose, liberated fructose and undesired oligosaccharides; reacting the so-purified dextran, having an average molar mass of from 2000 to 4000, with freshly precipitated iron(III) hydroxide and, if desired, further purifying the same.

In this manner, one succeeds in preparing a water soluble iron dextran having an iron content of from 27 to 33 percent by weight and an average molar mass of the dextran component of from 2000 to 4000.

The reaction mixture is preferably maintained at from 290 to 300 K. and a pH value in the range of 5 to 6.5. Both parameters have an influence on the structure of the resulting products.

According to the classification of the "Enzyme Commission", enzymes which transfer the D-glucopyranosyl group of sucrose to suitable acceptors are designated as $\alpha(1\rightarrow 6)$-D-glucosyl transferase. An extracellular enzyme of the kind is dextran sucrase (E.C. 2.4.1.5) which is formed by specific kinds of bacteria of the lactobacilli species, for example, Leuconostoc mesenteroides, in particular the strain B-512, Leuconostoc dextranicum, Streptococcus and lactobacillus. When preparing native dextran, sucrose serves primarily as acceptor and acts as chain initiator for a chain polymerization in which by virtue of continuous transfer of D-glucopyranosyl groups from the sucrose to the growing chain of the polysaccharide, dextrans having molar masses of several millions are formed, while, at the same time, a fructose molecule is liberated for each reacted molecule of sucrose.

If one uses in this reaction other mono- di- or tri-saccharides as acceptor, oligosaccharides are produced to a minor extent at the expense of the dextran. When employing glucose as acceptor, about 78 percent native dextran and, as by-product, about 13 percent di- and oligosaccharides up to IM-12. are produced. (Robyt and Eklund, Carbohydrate Research 121 (1983) 279–286). Typically, the oligosaccharides are produced in decreasing amounts with increasing degree of polymerization.

It is possible under the reaction conditions of the subject invention to control the transfer of glucosyl groups from sucrose to glucose such that no native dextran is produced, but the iso-malto-oligosaccharides having from 15 to 25 anhydroglucose units are formed at high yield. Surprising is hereby that the iso-malto-oligosaccharides are no longer formed in decreasing amounts with increasing degree of polymerization, but that, depending on the reacted amount of sucrose, a specific degree of polymerization is preferably obtained.

According to the process of this invention, it is recommendable for obtaining a high yield of the desired iso-malto-oligosaccharides to add the aqueous solution of sucrose continuously at such at rate that the amount of enzyme can immediately convert the amount of sucrose being fed thus avoiding an accummulation of sucrose in the reaction mixture which may lead to the uncontrolled formation of high molecular weight dextran. At all events, the part by weight of fructose of the carbohydrate dry substance of the reaction mixture should not exceed 25 percent at the equilibrium condition of the continuous reaction.

Instead of the purified dextran-sucrase, also the mixture comprising the enzyme and the bacteria which produce said enzyme may be employed.

The synthesis may be described as follows:

glucose + n sucrose 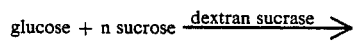

iso-malto-(n + 1)-saccharide + n fructose whereby n represents the number of moles of the sucrose, the D-glucopyranosyl groups of which serve for forming the low molecular weight dextran, while a corresponding mole number of fructose is liberated.

This reaction may be controlled according to the invention in such a manner that iso-malto-oligo- or polysaccharides of the desired molecular weight are obtained. Under the specified conditions of temperature and hydrogen ion concentration, the resulting molecular weight depends on the molar amount of the acceptor, based on a specific enzyme activity in the solution, and the mole ratio of the total amount of sucrose added to the acceptor.

The enzyme activity unit U (=Unit) is the amount of the $\alpha(1\rightarrow 6)$-D-glucosyl transferase which converts 1 $\mu$mol sucrose per minute at a pH of 5.2 and 298 K. If more sucrose is fed than the present enzyme activity can convert, the control of the size of the molecules will no longer be possible.

If an enzyme activity of 1000 U is taken as basis, the desired oligosaccharide mixture, having an average molecular weight of from about 2000 to 4000, will be obtained at an overall sucrose addition of 1000 mol and from 100 to 500 mmol, in particular from 200 to 500 mmol, glucose per 1000 units.

It is thus possible in a few preliminary tests with changing molar amounts of glucose within the specified ranges at predetermined activity of the $\alpha(1\rightarrow 6)$-D-glucosyl transferase (e.g. 1,000 U) and a constant amount of sucrose (e.g. 1,000 mmol), which is added to such an extent that it is directly converted by the enzyme, to control the linkage of the D-glucose pyranosyl groups of the sucrose to the glucose as acceptor in such a manner that fractions of each of the desired iso-malto-oligo- or polysaccharides having a narrow molecular weight distribution may be synthesized at high yield.

It is possible to provide the entire necessary amount of glucose, or, while observing the other reaction conditions, in particular the concentration ratios, to continuously replace the glucose to the extent to which it is consumed as acceptor. It is also possible to conduct the synthesis reaction continuously. An unexpected advantage of the process of the invention is that the carbohydrate content in the dry substance of the reaction mixture may be very high, in that it amounts to from 30 to 50 percent, in particular from 40 to 50 percent.

Although sterile operating conditions are observed in the enzymatic synthesis according to the invention, as is, for example, conventional in the synthesis of native dextran, antimitotics (mytosis inhibitors) may be added to the reaction mixture, such as sulfurous acid, in amount of up to 1000 mg/kg, in particular from 400 to 600 mg/kg, in order to avoid the undesirable growth of yeast.

The recovery of the dextrans having an average molecular weight of from 2000 to 4000 from the reaction mixture by separation of the non-reacted glucose, the liberated fructose and the iso-malto-oligosaccharides having less than 6 anhydroglucose units may be effected according to methods known per se, such as by precipitation-fractionation with ethanol.

A very suitable method for separating the by-products has proved to be a separation by chromatography in a column filled with a strongly acid cation exchanger.

For preparing the iron dextran, an aqueous suspension of the iso-malto-oligosaccharide mixture is heated with freshly precipitated iron(III) hydroxide to temperatures of up to 373 K. until the Iron(III) hydroxide is dissolved. It is recommendable to carry out this reaction in the presence of citric acid or alkali citrate, as is known per se from DE-PS 17 68 912.

For removing anions or cations which are still present in the solution of the iron dextran obtained after the reaction, the latter is subjected to the action of cation- and anion-exchangers.

EXAMPLE

Iron(III) hydroxide was precipitated by adding drop by drop a solution of 28 g soda, dissolved in 600 ml water, to 250 ml of an aqueous solution of 43 g iron(III) chloride hexahydrate. The iron(III) hydroxide was filtered and washed with distilled water. The iron(III) hydroxide was passed into a 1 liter stirrer flask and mixed with 15 g of the oligosaccharide mixture having an average molar mass of 3000 g/mol, obtained by chromatography, and with 0.5 g citric acid.

After addition of 9 ml of a 20 percent-NaOH solution, the mixture was stirred at 368 to 373 K. until the iron-(III)-hydroxide was completely dissolved.

The dark red solution of the resulting iron dextran was cooled down to room temperature and was desalted by means of ion-exchangers.

After a sterile filtration, the solution was concentrated by evaporation up to a content of 10 percent iron/ml and filled in a sterile manner in ampullas.

The iron content was 29.5 percent, based on the dry substance.

The so-obtained iron dextran solution was examined in respect of toxicity according to the British Veterinary Codex of 1965.

MM I-mice (breed: Winkelmann Paderborn) having an average weight of 20 g were used for the test.

The test substance, in the examined dosage of 0.25 ml/animal, caused light ataxiae immediately after termination of the injection which, however, completely eased off within 1 hour p.i.. No other symptoms were found throughout the remaining post observation period. Mortalities did not occur.

Example 2

7.3 kg crystalline glucose were dissolved at 298 K. in 16 liters of an aqueous solution of the enzyme dextran sucrase which had an activity of 5400 U/l. The pH value of the solution was 5.4 2.6 kg/h of a 40 percent-sucrose solution having a pH of 5.4 were continuously pumped into said solution. The addition of the sucrose was terminated after 48 hours and the enzyme was deactivated after 2 further hours by heating the reaction mixture to 70° C.

The mono- and disaccharide components were separated from a sample of the reaction mixture by gel chromatography and the mean value $M_n$, of the molecular weight of the oligosaccharide fraction was determined by the Somogyi-Phosphate Method (Methods in Carbohydrate Chemistry, Vol. I, (1962), p. 384–386). It was determined to be $M_n=2540$, which corresponds to an average degree of polymerization of 15.7 anhydroglycose units.

The part by weight of fructose in the carbohydrate dry substance was 45.0 percent, the glucose content 3.6 percent. 45 liters of this saccharide solution were placed in a chromatography separating plant containing 400 liters of a strongly acid cation-exchanger resin loaded with sodium ions and the individual saccharides were eluted from the column by adding 43 liters of distilled water per hour.

After a preliminary run of 60 liters, an iso-malto-oligo-saccharide mixture, having an average molar mass of 300 g/mol, was eluted from the separating column within the next 22 liters.

TEST REPORT

A litter of pigs was divided into two control groups, each comprising 4 animals. The one group was injected on the third day after birth each with 2 ml iron dextran according to BG-PS 1 200 902, the other group each with 2 ml iron dextran according to the invention. The occurring discoloration of the tissue at the injection spot disappeared after one day in the case of all animals which had been injected with the iron dextran according to the invention, while it was still clearly visible in the case of the pigs that were injected with the commercially available iron dextran. The discoloration disappeared only on the second day after the injection of the last-mentioned pigs. This result proves that iron originating from the iron dextran according to the invention is consumed more rapidly by the blood-forming tissue than that of the commercially available iron dextran.

I claim:

1. A process for the manufacture of water soluble iron dextran having an iron content of from 27 to 33 percent by weight and an average molar mass of the dextran component of from 2000 to 4000, characterized by adding to an aqueous solution containing more than 200 mmol D-glucose per 1000 U$\alpha$(1→6)-D-glucosyl transferase, at from 265 to 310 K. and a pH value of from 4.5 to 8, an aqueous sucrose solution in such an amount that the mole ratio of sucrose to glucose is from 2.0 to 5.0; separating, after the consumption of the sucrose, liberated fructose and undesirable oligosaccharides; reacting the so-purified dextran with freshly precipitated iron(III) hydroxide and optionaly further purifying the same.

2. A process according to claim 1, characterized in that the aqueous glucose solution contains from 400 to 600 mmol glucose per 1000 U enzyme.

3. A process according to claim 1, characterized in that the reaction is conducted at from 290 to 300 K.

4. A process according to claim 1, characterized in that the pH value of the reaction mixture is from 5 to 6.5.

5. A process according to claim 1, characterized in that the mole ratio of sucrose to glucose is from 3.0 to 4.0.

6. A process according to claim 1, characterized by adding the sucrose solution continuously.

7. A process according to claim 1, characterized by adding the sucrose solution at such a rate that the sucrose is directly converted by the $\alpha$(1→6)-D-glucosyl transferase.

8. A process according to claim 1, characterized in that the dry weight of the carbohydrate content of the reaction mixture is from 30 to 50 percent.

9. A process according to claim 1, characterized by using as $\alpha$(1→6)-D-glucosyl transferase the dextran sucrase produced by the bacterium *Leuconostoc mesenteriodies* strain B-512.

10. A process according to claim 1, characterized by using as $\alpha$(1→6)-D-glucosyl transferase the dextran sucrase produced by the bacterium *Leuconostoc dextranicum*.

11. A process according to claim 1, characterized by continuously replacing the D-glucose, to the same extent as it is consumed as acceptor.

12. A process according to claim 1, characterized by adding to the reaction mixture antimitotics to avoid undesired yeast growth.

13. A process according to claim 12, characterized by adding sulfurous acid in amounts of up to 1000 mg/kg.

14. A process according to claim 1, characterized by separating from the mixture of the mono-, di, and oligosaccharides the dextrans having an average molar mass of from 2000 to 4000 by precipitation-fractionation or chromatography.

15. A process according to claim 1, characterized by heating an aqueous suspension of the iso-malto-oligosaccharide mixture and the precipitated iron(III) hydroxide to temperatures of up to 373 K. until the iron(III)hydroxide is dissolved.

16. A process according to claim 15, characterized by conducting the reaction in the presence of citric acid or alkali citrate.

17. A process according to claim 15, characterized by subjecting the solution of the iron dextran obtained after the reaction to the action of cation and anion exchangers.

* * * * *